(12) United States Patent
McNally et al.

(10) Patent No.: US 6,534,325 B1
(45) Date of Patent: Mar. 18, 2003

(54) IMMUNOASSAY FOR THE DETECTION OF AMPHETAMINES, METHAMPHETAMINES AND METHYLENEDIOXY DESIGNER AMPHETAMINES

(75) Inventors: Alan J. McNally, Carmel, IN (US); Huiru Zhao, Carmel, IN (US); Krystyna Goc-Szkutnicka, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/608,524

(22) Filed: Jun. 30, 2000

(51) Int. Cl.$^7$ .................... G01N 33/546; G01N 33/533; G01N 33/534; G01N 33/535
(52) U.S. Cl. .................... 436/533; 435/7.93; 436/545; 436/546; 436/816
(58) Field of Search .................... 435/7.93; 436/545, 436/546, 533, 816

(56) References Cited

U.S. PATENT DOCUMENTS

| | | | |
|---|---|---|---|
| 5,262,333 A | 11/1993 | Heiman et al. | 436/537 |
| 5,501,987 A | 3/1996 | Ordonez et al. | 436/534 |
| 5,618,926 A | 4/1997 | Salamone et al. | 530/403 |
| 5,976,812 A | 11/1999 | Huber et al. | 435/7.1 |

FOREIGN PATENT DOCUMENTS

| | | | | |
|---|---|---|---|---|
| EP | 0375422 A2 | 6/1990 | | G01N/33/535 |
| EP | 0574782 A2 | 12/1993 | | G01N/33/94 |

OTHER PUBLICATIONS

Ward, Cynthia et al., "Radioimmunoassay for the Dual Detection of Amphetamine and Methamphetamine," Journal of Forensic Sciences, 1486–1496.

Zhao, Huiru et al., "Profiles of Urine Samples Taken from Ecstasy Users at Rave Parties: Analysis by Immunoassays, HPLC, and GC–MS," Journal of Analytical Toxicology, vol. 25, May/Jun. 2001, 258–269.

Cody, John T. et al., "Fluorescence Polarization Immunoassay Detection of Amphetamine, Methamphetamine, and Illicit Amphetamine Analogues," Journal of Analytical Toxicology, vol. 17, Jan./Feb 1993, 26–30.

Ruangyuttikam, Werawan et al., "Comparison of Three Commerical Amphetamine Immunoassays for Detection of Methamphetamine, Methylenedioxyamphetamine, Methylenedioxymethamphetamine, and Methylenedioxyethylamphetamine," Center for Human Toxicology, Department of Pharmacology and Toxicology, University of Utah, College of Pharmacy, Salt Lake City, Utah 84112, 229–233.

John T. Cody et al. "Fluorescence Polarization Immunoassay Detection of Amphetamine, Methamphetameine, and Illicit Amphetamine Analogues" Journal of Analytical Toxicology, vol. 17, Jan./Feb. 1993 pp. 26–30.

G.W. Kunsman, et al. "Application of the Syva EMIT and Abbott TDx Amphetamine Immunoassays to the Detection of 3,4–Methylenedioxymethamphetamine (MDMA) and 3,4—Methylenedioxythamphetamine (MDEA) in Urine" Journal of Analytical Toxicology, vol. 14, May/Jun. 1990 pp. 149–153.

Alphonse Poklis et al. "Emit–d.a.u. Monoclonal Amphetamine/Methamphetamine Assay.II. Detection of Methylenedioxyaphetamine (MDA) and Methylenedioxymethamphetamine (MDMA)" Forensic Science International, 59 (1993) pp. 63–70 Elsevier Scientific Publisher Ireland Ltd.

*Primary Examiner*—Mary E. Ceperley
(74) *Attorney, Agent, or Firm*—Marilyn L. Amick; Roche Diagnostics Corporation

(57) ABSTRACT

The present invention provides an immunoassay method for the highly sensitive detection of amphetamines, methamphetamines, and methylenedioxy designer amphetamines in urine samples. Commercially available reagents for the determination of amphetamines and methamphetamines are used with a calibrator comprising a known amount of a substance selected from the group consisting of methylenedioxy designer amphetamines.

14 Claims, 3 Drawing Sheets amphetamine 3,4-methylenedioxymethamphetamine (MDMA)

3,4-methylenedioxyamphetamine (MDA)

3,4-methylenedioxyethylamphetamine (MDEA)

methamphetamine

N-methyl-1-(3,4-methylenedioxyphenyl)-2-butanamine (MBDB)

4-hydroxy-3-methoxymethamphetamine (HMMA)

3,4-methylenedioxyphenyl-2-butanamine (BDB)

IMMUNOASSAY FOR THE DETECTION OF AMPHETAMINES, METHAMPHETAMINES AND METHYLENEDIOXY DESIGNER AMPHETAMINES

BACKGROUND OF THE INVENTION

This invention relates generally to the field of measuring an analyte in a liquid medium. More specifically, it relates to an assay for the measurement of a drug of abuse in a biological sample. In particular, the invention relates to a highly sensitive immunoassay method for the detection of amphetamines, methamphetamines, structurally related drugs such as 3,4-methylenedioxymethamphetamine (MDMA) and metabolites of these drugs in biological samples.

The amphetamine analogues of methylenedioxyphenylalkylamines are a series of compounds referred to as "designer" amphetamines. As represented in FIG. 1, these psychotropic drugs are ring-substituted derivatives chemically related to mescaline. They include methylenedioxyamphetamine (MDA), methylenedioxymethamphetamine (MDMA, also known as Ecstasy), methylenedioxyethylamphetamine (MDEA), N-methylbenzodioxazolylbutanamine (MBDB) and benzodioxazol-5'-yl-2-butanamine (BDB), the most common of these being MDMA.

MDA has been shown to be the metabolite of both MDMA and MDEA. Several animal studies have shown that MDMA is metabolized by N-demethylation, deamination, O-methylation and O-conjugation to glucuronide and/or sulfate metabolites. Detected in urine are the parent drug (MDMA), 3,4-methylenedioxylamphetamine (MDA), 4-hydroxy-3-methoxymethamphetamine (HMMA), 3-hydroxy-4-methoxymethamphetamine, 4-hydroxy-3-methoxyphenylacetone, 3,4-methylenedioxyphenylacetone and 3,4-dihydroxyphenylacetone. Most of these metabolites are also present in the blood.

Urine and blood are the most commonly studied biological matrices for MDMA, MDA, MDEA and MBDB and are well documented in the literature. Determination of these designer drugs in other biological specimens such as saliva, sweat and hair has been reported more recently. The parent drug is detected in higher concentrations than its metabolites in these matrices.

The abuse of these designer amphetamines is increasing throughout the world, and their detection by screening methods is becoming a more important issue. Zhao, H. et al., *J Anal. Toxicology Vol.* 25, PD 258–269(2001) found 71% of urine samples from rave party attendees contained MDMA or MDA alone or in combination with amphetamine or other designer amphetamines such as MDEA. Presently there are no commercial immunoassays designed specifically for the detection of these substances, and their detection therefore depends on the relative cross-reactivities they exhibit in the amphetamine or methamphetamine screening method used. In general, the cross-reactivity of the commercially available amphetamine and methamphetamine assays toward many of these compounds is low which suggests the possibility that some positive samples may go undetected.

In testing for drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such a β-galactosidase and peroxidase, fluorescent molecules such as fluorescein compounds, radioactive compounds such as $^{125}$I, and microparticles are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

Gas chromatography/mass spectrometry (GC/MS) is highly specific and has been described for the simultaneous detection of MDMA, MDA, amphetamine, methamphetamine, MDEA and their metabolites. GC/MC analysis is usually required for confirmation and verification of the results of an immunological assay or a suspected diagnosis. In this technique, MDMA or designer drugs are extracted in solid phase, then derivatized and analyzed via GC/MS.

In U.S. Pat. No. 5,501,987 issued Mar. 26, 1996, Ordonez et al. describe a dual analyte immunoassay for the determination of amphetamine and methamphetamine using a single labeled binding partner capable of cross reacting at differing sensitivities to antibodies derived from conjugate derivatives of amphetamine and methamphetamine. Calibrators used are prepared by adding d-amphetamine to drug-free, normal human urine.

SUMMARY OF THE INVENTION

Quite surprisingly, it has been discovered that a highly specific immunoassay method for the detection of amphetamines, methamphetamines, structurally related drugs such as 3,4-methylenedioxymethamphetamine (MDMA) and their metabolites in urine samples can be achieved by the use of a calibrator comprising a substance selected from the group consisting of methylenedioxy designer amphetamines in drug free, normal human urine and an antibody having specificity for amphetamine or methamphetamine and cross-reactivity with amphetamine analogues of methylenedioxyphenylalkylamines.

In the method of the invention, a sample suspected of containing amphetamine, methamphetamine or a structurally related drug is combined with an antibody having specificity for amphetamine or methamphetamine and a labeled binding partner which can interact with the combination of antibody and its corresponding analyte so as to detect the presence of the analytes at selected cutoff levels either alone or in combination. The particular antibody or antibodies used must have cross-reactivity with amphetamine analogues of methylenedioxyphenylalkylamines. This invention can be used with any type of immunoassay format, e.g., turbidometric agglutination assay, radioimmunoassay, enzyme immunoassay, or fluorescent polarization immunoassay. Especially preferred is the use of the present invention with agglutinometric formats susceptible to an instrumental method for the measurement of the changes brought about by the agglutination reaction. Both manual as well as automated apparatus testing may be suitably employed for such agglutinometric analysis. Typically, automated instrumentation will operate utilizing a multiplicity of reagent containers or reservoirs from which will be pipetted the appropriate amount of each reagent for addition to the sample. For immunoassays such as the subject agglutination assay, this will usually involve at least two such containers; typically, one for an antibody reagent and the other for the microparticles bound with the corresponding ligand. Additional containers or reservoirs may be present in some instruments containing diluent, buffers or other additives for appropriate treatment of the sample.

The clinical analyzer pipettes the onboard reagents and samples into one cuvette where the competitive agglomeration reaction occurs and measurement of the turbidity is made. For example, using the HITACHI 917 analyzer (Roche Diagnostics) and the ABUSCREEN® OnLine Amphetamines reagent kit (Roche Diagnostics, Cat. No. 1985965), urine sample is pipetted with sample diluent into the cuvette, followed immediately by the appropriate amount of antibody reagent and mixing. An initial spectrophotometer reading is taken. Then the appropriate quantity of microparticle reagent is transferred to the cuvette and the reaction mixed. After a brief incubation, a final turbidity measurement is made. The overall change in turbidity (absorbance) in the reaction is compared to a calibration curve and results reported in ng/ml.

The present invention also encompasses a reagent test kit which comprises, in packaged combination, an antibody specific for amphetamine, an antibody specific for methamphetamine, a complex comprising a ligand of amphetamine or an amphetamine derivative coupled to a labeling moiety, and a calibrator comprising a known amount of a substance selected from the group consisting of methylenedioxy designer amphetamines. Such a test kit provides reagents for an assay with enhanced clinical sensitivity for MDMA and structurally-related compounds.

DETAILED DESCRIPTION OF THE INVENTION

Figure 1:
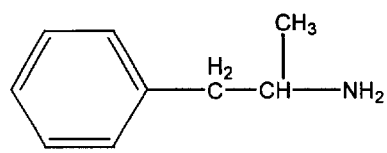
FIG. 1 shows the structures of amphetamine, methamphetamine and 3,4-methylenedioxy designer drugs.
Figure 1:
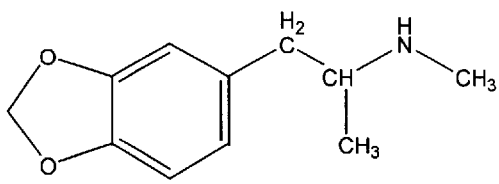
Figure 1:
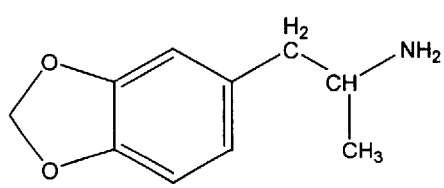
Figure 1:
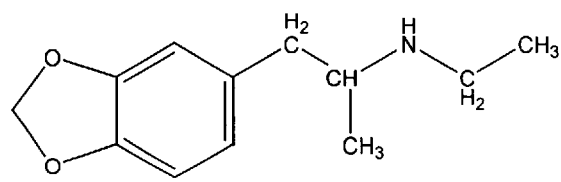
Figure 1:
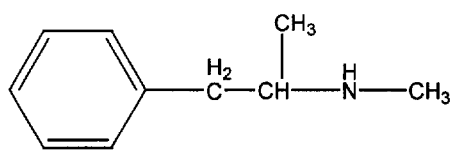
Figure 1:
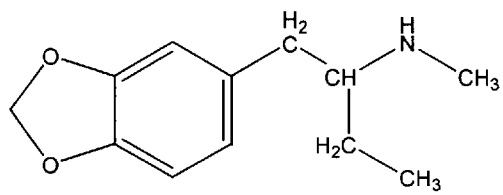
Figure 1:
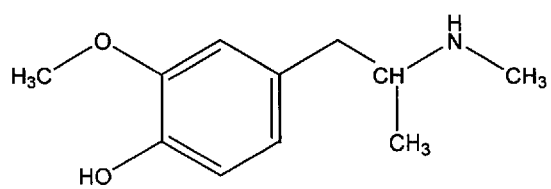
Figure 1:
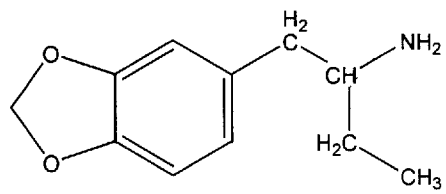

Commercial immunoassay kits for determination of MDMA are currently not available. The only way to determine MDMA via immunoassay is to use reagents or a reagent kit for determining amphetamine or methamphetamine comprising an amphetamine antibody and methamphetamine antibody having high cross-reactivity with MDMA and using amphetamine or methamphetamine as a calibrator. In the present invention, a substance selected from the group consisting of methylenedioxy designer amphetamines is used to calibrate a commercially available assay using antibodies for amphetamine and methamphetamine. The use of a methylenedioxy designer amphetamine calibrator significantly increased the clinical sensitivity for MDMA, MBDB, MDA, MDE, and BDB without significant increase for medications such as β-hydroxyphenylamines, e.g., ephedrine, pseudoephedrine, phentamine, tyramine and phenylpropanolamine (PPA).

Abbreviations used:

| | |
|---|---|
| AMP | amphetamine |
| BDB | (±)-(3,4-methylenedioxyphenyl)-2-butanamine |
| HMMA | 4-hydroxy-3-methoxymethamphetamine |
| MAMP | methamphetamine |
| MBDB | (±)-N-methyl-1-(3,4-methylenedioxyphenyl)-2-butanamine |
| MDA | (±)-3,4-methylenedioxyamphetamine |
| MDEA | (±)-3,4-methylenedioxyethylamphetamine |
| MDMA | (±)-3,4 methylenedioxymethamphetamine |
| NT | not tested |
| PPA | phenylpropanolamine |

Cross-reactivities of currently marketed assays for MDMA and MDA, according to published literature, as well as cross-reactivities using the method of the present invention are listed in the table below.

By "methylenedioxy designer amphetamines" is meant the group of amphetamine analogues of methylenedioxyphenylalkylamines including methylenedioxyamphetamine (MDA), methylenedioxymethamphetamine (MDMA, Ecstasy), methylenedioxyethylamphetamine (MDEA), N-methylbenzodioxazolylbutanamine (MBDB) and benzodioxazol-5'-yl-2-butanamine (BDB).

| Compound | Roche Hitachi AMP 500 ng/ml | Roche Integra AMPSC 500 ng/ml | Abbott TDX AMP/methAMP 1000 ng/ml | CEDIA DAU AMP 1000 ng/ml | Roche Hitachi AMP/MDMA 300 ng/ml |
|---|---|---|---|---|---|
| MDMA | 36% | 79% | 97% | 69% | 100.0% |
| MDA | 35.5% | 40% | 148% | 1.9% | 25.0% |
| MDEA | NT | NT | 42.7% | 2.4% | 15.0% |
| MBDB | NT | NT | (+) | NT | 70.0% |
| BDB | NT | NT | (+) | NT | 4.7% |
| d-AMP | 100% | 100% | 100% | 101% | 97.0% |
| l-AMP | 6% | 4.2% | 56.9% | 3.0% | 3.8% |
| d-MAMP | 82.2% | 12% | 97.8% | 100% | 300.0% |
| l-MAMP | 0.8% | 12% | 7.2% | 12% | 18% |
| dl-ephedrine | <0.1% | <0.1% | NT | 0.4% | <0.3% |
| l-PPA | 1.5% | 1.1% | NT | NT | 0.6% |
| HMMA | NT | NT | NT | NT | <0.3% |

Cutoff levels, which are indicated in the above chart for each method, are the concentration of drugs in the sample required for the test to determine a positive result.

EXAMPLE 1

1. Preparation of Antibody Reagent

A first reagent was prepared according to the directions accompanying the ABUSCREEN® OnLine HS Amphetamine/MDMA reagent kit (Roche Diagnostics, Cat. No. 1986619). The reagent contained amphetamine and methamphetamine monoclonal antibodies (mouse) in a buffer with bovine serum albumin and a preservative.

EXAMPLE 2

Preparation of Microparticle Reagent

A second reagent was prepared according to the directions accompanying the ABUSCREEN® OnLine HS Amphetamine/MDMA reagent kit (Roche Diagnostics, Cat. No. 1986619). The reagent contained an amphetamine derivative conjugated to latex microparticles in a buffer with a preservative.

EXAMPLE 3

Preparation of MDMA Calibrator

Calibrators were prepared according to the directions accompanying the ABUSCREEN® OnLine Preciset® MDMA calibrators (Roche Diagnostics, Cat. No. 4745556). The calibrator solutions contained 3,4-methylenedioxymethamphetamine in human urine with a preservative. Final concentrations of the calibrators were 0, 150, 300 and 600 ng/ml.

EXAMPLE 4

Assay using MDMA Calibrator

Figure 2:
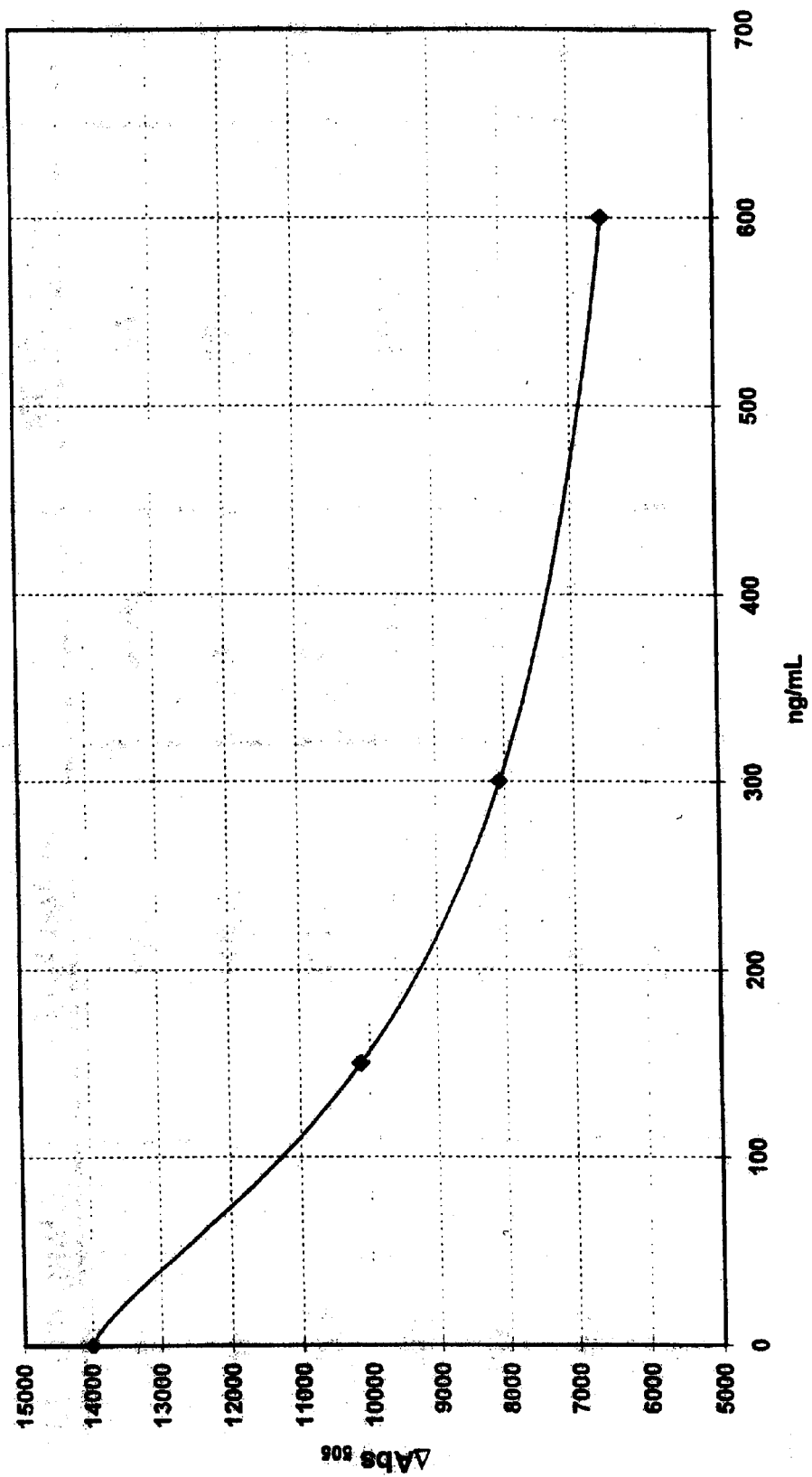
FIG. 2 is a dose response curve generated using the assay of the present invention comprising an antibody specific for amphetamine, an antibody specific for methamphetamine and calibrators comprising known amounts of MDMA.

Calibrators or reference samples prepared according to Example 3 were assayed according to the directions accompanying the OnLine reagent kit using an HITACHI 917 analyzer (Roche Diagnostics) and a cutoff value of 300 ng/ml. Parameters used were 10 µl sample, 160 µl antibody reagent and 90 µl microparticle reagent. The reaction was run monochromatically (505 nm) in the endpoint (read point 19–33). The dose response curve is shown in FIG. 2, with the change in absorbance at 505 nm plotted on the y-axis and MDMA concentration plotted on the x-axis.

Example 5

Assay using MDA Calibrator

Figure 3:
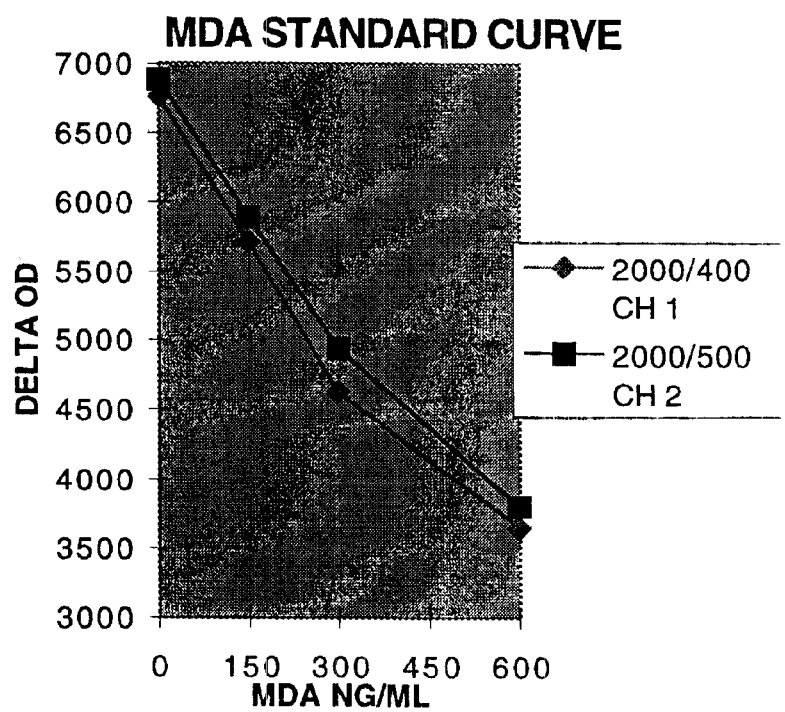
FIG. 3 is a dose response curve generated using the assay of the present invention comprising an antibody specific for amphetamine, an antibody specific for methamphetamine and calibrators comprising known amounts of MDA.

Calibrators or reference samples prepared as described in Example 3 except using MDA in place of MDMA were assayed according to the directions accompanying the OnLine reagent kit using an HITACHI 717 analyzer (Roche Diagnostics). Parameters used were 15 µl sample, 170 µl antibody reagent and 80 µl microparticle reagent. The reaction was run monochromatically (505 nm) in the endpoint (27–50). The dose response curve obtained is shown in FIG. 3, with the change in absorbance at 505 nm plotted on the y-axis and MDA concentration plotted on the x-axis.

Cross-reactivities observed when MDA was used as a calibrator were as follows:

| Compound | Roche Hitachi AMP/MDMA 300 ng/ml |
|---|---|
| MDMA | 81.0% |
| MDA | 100.0% |
| d-AMP | 319.0% |
| l-AMP | 15.2% |
| d-MAMP | 269.0% |
| l-MAMP | 24.7% |
| dl-ephedrine | 0.34% |
| l-PPA | 6.2% |

EXAMPLE 6

Assay of Urine Samples

Urine specimens suspected of containing amphetamine, methamphetamine or methylenedioxy designer amphetamines were treated according to the procedure described in Example 4 using MDMA calibrators at levels of 0, 150, 300 and 600 ng/ml. Results were obtained by comparing the change in absorbance at 505 nm for an unknown sample with that obtained with the calibrators of known concentration. Results obtained on 72 urine specimens had 100% agreement with a reference chromatographic method for the detection of designer amphetamines.

What is claimed is:

1. A method for determining amphetamine, methamphetamine, and methylenedioxy designer amphetamine analytes in a biological sample suspected of containing one or more of the analytes, the method comprising the steps of:

a. combining the sample with a first antibody specific for amphetamine and having cross-reactivity with methylenedioxy designer amphetamines, a second antibody specific for methamphetamine and having cross-reactivity with methylenedioxy designer amphetamines, and a complex comprising an analog of amphetamine or an amphetamine derivative coupled to a labeling moiety, whereby the analytes and the analog competitively bind to the antibodies, b. measuring the presence or amount of the labeling moiety which remains bound or unbound to said antibodies as a result of competitive displacement by said analytes, c. comparing the presence or amount of the labeling moiety measured in step (b) with the presence or amount of labeling moiety measured in a reference sample containing a known amount of a substance selected from the group consisting of methylenedioxy designer amphetamines, said reference sample being treated according to steps (a) and (b), and d. correlating the comparison made in step (c) to the presence or amount of the analytes in the sample.

2. The method of claim 1, wherein said sample is urine.

3. The method of claim 2, wherein said substance is MDMA.

4. A method for determining amphetamine, methamphetamine, and methylenedioxy designer amphetamine analytes in a biological sample suspected of containing one or more of the analytes, the method comprising the steps of:

a. combining the sample with an antibody selected from the group consisting of antibodies specific for amphetamine and having cross-reactivity with methylenedioxy designer amphetamines and antibodies specific for methamphetamine and having cross-reactivity with methylenedioxy designer amphetamines, and further with a complex comprising an analog of amphetamine or an amphetamine derivative coupled to a labeling moiety, whereby the analytes and the analog competitively bind to the antibody, b. measuring the presence or amount of the labeling moiety which remains bound or unbound to said antibody as a result of competitive displacement by said analytes, c. comparing the presence or amount of the labeling moiety measured in step (b) with the presence or amount of labeling moiety measured in a reference sample containing a known amount of a substance selected from the group consisting of methylenedioxy designer amphetamines, said reference sample being treated according to steps (a) and (b), and d. correlating the comparison made in step (c) to the presence or amount of the analytes in the sample.

5. The method of claim 4, wherein said sample is urine.

6. The method of claim 5, wherein said substance is MDMA.

7. A kit for conducting an assay for the determination of an analyte selected from the group consisting of amphetamine, methamphetamine, and methylenedioxy designer amphetamines in a biological sample comprising in packaged combination:

a. a first antibody specific for amphetamine and having cross-reactivity with amphetamine analogues of methylenedioxyphenylalkylamine, b. a second antibody specific for methamphetamine and having cross-reactivity with amphetamine analogues of methylenedioxyphenylalkylamine, c. a complex comprising a ligand of amphetamine or an amphetamine derivative coupled to a labeling moiety, and d. a calibrator comprising a known amount of a substance selected from the group consisting of methylenedioxy designer amphetamines.

8. The method of claim 7, wherein said substance is MDMA.

9. A kit for conducting an assay for the determination of an analyte selected from the group consisting of amphetamine, methamphetamine, and methylenedioxy designer amphetamines in a biological sample comprising in packaged combination:

a. an antibody selected from the group consisting of antibodies specific for amphetamine and having cross-reactivity with amphetamine analogues of methylenedioxyphenylalkylamine and antibodies specific for methamphetamine and having cross-reactivity with amphetamine analogues of methylenedioxyphenylalkylamine, b. a complex comprising a ligand of amphetamine or an amphetamine derivative coupled to a labeling moiety, and c. a calibrator comprising a known amount of a substance selected from the group consisting of methylenedioxy designer amphetamines.

10. The method of claim 9, wherein said substance is MDMA.

11. The method of claim 1, wherein the methylenedioxy designer amphetamine analyte is 3,4-methylenedioxymethamphetamine (MDMA).

12. The method of claim 4, wherein the methylenedioxy designer amphetamine analyte is 3,4-methylenedioxymethamphetamine (MDMA).

13. The method of claim 1, wherein the first and second antibodies have cross-reactivity with 3,4-methylenedioxymethamphetamine (MDMA).

14. The method of claim 4, wherein the antibody has cross-reactivity with 3,4-methylenedioxymethamphetamine (MDMA).

* * * * *